US012478427B2

(12) United States Patent
Coulombe et al.

(10) Patent No.: US 12,478,427 B2
(45) Date of Patent: Nov. 25, 2025

(54) CONTACT PRESSURE ASSESSMENT FOR CRYOBALLOON ABLATION CATHETERS

(71) Applicant: Medtronic CryoCath LP, Toronto (CA)

(72) Inventors: Nicolas Coulombe, Anjou (CA); Rachid Mahrouche, Cote St-Luc (CA); Louis Jacob, Laval (CA); Dan Wittenberger, Blainville (CA); Martin Lacharite, Vaudreuil-Dorion (CA); Jean-Pierre Lalonde, Candiac (CA)

(73) Assignee: Medtronic CryoCath LP, Toronto (CA)

( * ) Notice: Subject to any disclaimer, the term of this patent is extended or adjusted under 35 U.S.C. 154(b) by 717 days.

(21) Appl. No.: 17/814,405

(22) Filed: Jul. 22, 2022

(65) Prior Publication Data

US 2023/0053149 A1 Feb. 16, 2023

Related U.S. Application Data

(60) Provisional application No. 63/231,331, filed on Aug. 10, 2021.

(51) Int. Cl.
*A61B 18/14* (2006.01)
*A61B 18/02* (2006.01)
*A61B 18/00* (2006.01)

(52) U.S. Cl.
CPC .......... *A61B 18/1492* (2013.01); *A61B 18/02* (2013.01); *A61B 2018/0022* (2013.01);
(Continued)

(58) Field of Classification Search
CPC ............ A61B 18/02; A61B 2018/0022; A61B 2018/0212; A61B 2018/0262;
(Continued)

(56) References Cited

U.S. PATENT DOCUMENTS

| | | | | |
|---|---|---|---|---|
| 9,808,301 | B2 | 11/2017 | Abboud et al. | |
| 2007/0032783 | A1 * | 2/2007 | Abboud | A61B 18/02 606/22 |
| 2014/0276698 | A1 * | 9/2014 | Wittenberger | A61B 18/1492 606/21 |

OTHER PUBLICATIONS

International Search Report and Written Opinion for Application No. PCT/CA2022/051204 dated Nov. 10, 2022 (8 pages).

* cited by examiner

*Primary Examiner* — Jon Eric C Morales
(74) *Attorney, Agent, or Firm* — Michael Best & Friedrich LLP

(57) ABSTRACT

A method of ablating tissue includes positioning a treatment device proximate to a target tissue area. The treatment device has an expandable treatment element. The expandable treatment element is inflated with a refrigerant during an inflation phase such that at least a portion of the expandable treatment element is in contact with the target tissue area. A first pressure measurement of the inflated expandable treatment element is recorded and compared to a predetermined pressure threshold. The refrigerant is circulated within the expandable treatment element during an ablation phase to reduce a temperature of the target tissue area to a temperature sufficient to cryoablate the target tissue area. A second pressure measurement of the expandable treatment element is recorded during the ablation phase and compared to the predetermined pressure threshold.

16 Claims, 6 Drawing Sheets

(52) U.S. Cl.
CPC ................ *A61B 2018/0212* (2013.01); *A61B 2018/0262* (2013.01)

(58) Field of Classification Search
CPC ...... A61B 18/1492; A61B 2017/22051; A61B 2018/00041; A61B 2018/00351; A61B 2018/00577; A61B 2018/00994; A61B 2018/0268; A61B 2018/0293; A61M 2025/0024; A61M 25/0113; A61M 25/1011; A61M 25/1018; A61M 25/10184; A61M 25/10185; A61M 25/10187
See application file for complete search history.

CONTACT PRESSURE ASSESSMENT FOR CRYOBALLOON ABLATION CATHETERS

CROSS-REFERENCE TO RELATED APPLICATION

The present application is related to and claims benefit under 35 U.S.C. § 119(e) from U.S. Provisional Patent Application Ser. No. 63/231,331, filed Aug. 10, 2021, entitled "CONTACT PRESSURE ASSESSMENT FOR CRYOBALLOON ABLATION CATHETERS," the entire contents of which being incorporated herein by reference.

TECHNICAL FIELD

The present invention relates to a device, system, and method for performing a variety of treatment procedures safely with a single treatment device. For example, a system is provided that includes a treatment device with a pressure monitoring tube disposed within an expandable treatment element that is configured to continuously monitor a degree of contact pressure between the balloon element and a target tissue area, which enhances balloon-tissue contact, treatment efficacy, and patient safety.

BACKGROUND

Cardiac arrhythmia, a group of disorders in which the heart's normal rhythm is disrupted, affects millions of people. Certain types of cardiac arrhythmias, including ventricular tachycardia and atrial fibrillation, may be treated using one or more energy modalities, such as cryoablation, either endocardially or epicardially.

The effectiveness of an ablation procedure may largely depend on the quality of contact between the treatment element of the medical device and the cardiac tissue. Procedures such as pulmonary vein isolation (PVI) are commonly used to treat cardiac arrhythmias such as atrial fibrillation. In such a procedure, the treatment element, such as a cryoballoon, may be positioned at the pulmonary vein ostium in order to create a circumferential lesion surrounding the ostium. However, the success of this procedure depends largely on the quality of the lesion(s) created during the procedure and whether the cryoballoon has completely occluded the pulmonary vein. For example, a complete circumferential lesion is produced only when the cryoballoon has completely occluded the pulmonary vein. Incomplete occlusion, on the other hand, allows blood to flow from the pulmonary vein being treated, past the cryoballoon, and into the left atrium of the heart. This flow of warm blood may prevent the cryoballoon from reaching temperatures low enough to create permanent lesions in the targeted tissue. The creation of reversible lesions may not be sufficient to achieve electrical isolation and, as a result, the cardiac condition may be likely to reoccur.

When performing PVI, it also may be difficult to prevent the treatment element from moving too deep within the pulmonary vein when applying sufficient pressure through the device elongate body to ensure adequate contact between the treatment element and the pulmonary vein ostium. Ablating tissue within the pulmonary vein may lead to complications such as cardiac tamponade, in which the pericardial sac surrounding the heart fills will blood, and pulmonary vein stenosis. In currently known catheter systems, there is no means to provide feedback regarding the force or pressure exerted onto the cardiac tissue and/or adjacent collateral structures. Due to the tortuous path of the catheter and the interactions with the catheter's introducer sheath, valve, guidewire, or mapping catheter, the tactile feel of the operating physician can be misleading.

Additionally, treatment elements of different sizes, shapes, and configurations may all be required in a single ablation procedure. For example, an ablation procedure may involve PVI and linear ablation patterns. To achieve this, a physician may employ several different catheters having variations in the geometry and/or dimensions of the treatment element in order to produce the desired ablation pattern. Each device may have a unique geometry for creating a specific lesion pattern, with the multiple catheters being sequentially removed and replaced to create the desired lesions. However, exchanging the various devices during a procedure can cause inaccuracies or movement in the placement and location of the distal tip with respect to the targeted tissue, and may further add to the time required to perform the procedure and may increase the risk of patient injury and discomfort. Even if a single device includes a treatment element that is transitionable between configurations to provide a number of different ablation patterns, it may be physically challenging to transition the treatment element without displacing the device from the treatment site.

SUMMARY

The techniques of this disclosure generally relate to a system that includes a treatment device in communication with a console having a pressure sensor disposed therein. The console is configured to continuously monitor a degree of contact pressure between the balloon element and a target tissue area, which enhances balloon-tissue contact, treatment efficacy, and patient safety.

In one aspect, a method of ablating tissue includes positioning a treatment device proximate to a target tissue area. The treatment device has an expandable treatment element. The expandable treatment element is inflated with a refrigerant during an inflation phase such that at least a portion of the expandable treatment element is in contact with the target tissue area. A first pressure measurement of the inflated expandable treatment element is recorded during the inflation phase and compared to a predetermined pressure threshold. The refrigerant is circulated within the expandable treatment element during an ablation phase to reduce a temperature of the target tissue area to a temperature sufficient to cryoablate the target tissue area. A second pressure measurement of the expandable treatment element is recorded during the ablation phase and compared to the predetermined pressure threshold.

In another aspect, the method further includes calculating a difference between the first pressure measurement and the predetermined pressure threshold.

In another aspect, the method further includes assigning a first contact score based on the calculated difference. The assigned first contact score is indicative of a degree of tissue contact by the expandable treatment element during the inflation phase.

In another aspect, the method further includes calculating a difference between the second pressure measurement and the predetermined pressure threshold, and assigning a second contact score based on the calculated difference between the second pressure measurement and the predetermined pressure threshold. The assigned second contact score is indicative of a degree of tissue contact by the expandable treatment element during the ablation phase.

In another aspect, the method further includes determining whether undue force is being applied to the treatment device during at least one of the ablation phase and the inflation phase based, in part, on at least one of the first contact score and the second contact score.

In another aspect, the method further includes generating an alert if it is determined that undue force is being applied to the treatment device during at least one of the ablation phase and the inflation phase.

In another aspect, the method further includes at least one selected from the group consisting of adjusting a flow rate of the refrigerant if it is determined that undue force is being applied to the treatment device during at least one of the ablation phase and the inflation phase, and discontinuing the circulation of refrigerant if it is determined that undue force is being applied to the treatment device during at least one of the ablation phase and the inflation phase.

In another aspect, the method further includes determining whether the second contact score is indicative of inadequate tissue contact, generating an alert if the second contact score indicates inadequate tissue contact during at least one of the ablation phase and the inflation phase, and at least one of adjusting a flow rate of the refrigerant and discontinuing the circulation of refrigerant if the second contact score indicates inadequate tissue contact during at least one of the ablation phase and the inflation phase.

In yet another aspect, a system for ablating tissue includes a treatment device and a control unit. The treatment device includes an expandable treatment element and a pressure monitoring tube having a proximal portion and an opposite distal portion. The distal portion is partially disposed within the expandable treatment element. The control unit is in communication with the treatment device and includes processing circuitry configured to: initiate and transition between an inflation phase and an ablation phase, record a first pressure measurement of the expandable treatment element during the inflation phase and compare the first pressure measurement to a predetermined pressure threshold, and record a second pressure measurement of the expandable treatment element during the ablation phase and compare the second pressure measurement to the predetermined pressure threshold.

In another aspect, the processing circuitry is further configured to calculate a difference of each of the first pressure measurement and the second pressure measurement from the predetermined pressure threshold.

In another aspect, the control unit further includes a fluid supply reservoir in fluid communication with the expandable treatment element, and a pressure sensor configured to monitor a pressure of the expandable treatment element.

In another aspect, the inflation phase includes inflating the expandable treatment element such that the expandable treatment element is in contact with a target tissue area.

In another aspect, the ablation phase includes delivering refrigerant from the fluid supply reservoir to the expandable treatment element to treat the target tissue area.

In another aspect, the control unit is further configured to assign a first contact score based on a comparison of the calculated difference between the first pressure measurement and the predetermined pressure threshold to a predefined table, and assign a second contact score based on a comparison of the calculated difference between the second pressure measurement and the predetermined pressure measurement to the predefined table.

In another aspect, the processing circuitry is further configured to determine whether undue force is being applied to the treatment device during at least one of the ablation phase and the inflation phase based, in part, on at least one of the first contact score and the second contact score.

In another aspect, the processing circuitry is further configured to generate an alert if it is determined that undue force is being applied to the treatment device during at least one of the ablation phase and the inflation phase.

In another aspect, the processing circuitry is further configured to perform one operation selected from the group consisting of: adjust a flow rate of the refrigerant if undue force is being applied to the treatment device during the at least one of the ablation phase and the inflation phase; and discontinue the delivery of refrigerant if undue force is being applied to the treatment device during the at least one of the ablation phase and the inflation phase.

In another aspect, the processing circuitry is further configured to determine whether at least one of the first contact score and the second contact score is indicative of inadequate tissue contact.

In another aspect, the processing circuitry is further configured to: generate an alert if the at least one of the first contact score and the second contact score indicates inadequate tissue contact during at least one of the ablation phase and the inflation phase; and at least one of adjust a flow rate of the refrigerant and discontinue the circulation of refrigerant if the at least one of the first contact score and the second contact score indicates inadequate tissue contact during at least one of the ablation phase and the inflation phase.

In yet another aspect, a system for ablating tissue includes a treatment device and a control unit in communication with the treatment device. The treatment devices includes an expandable treatment element and a pressure monitoring tube. The pressure monitoring tube has a proximal portion and an opposite distal portion. The distal portion is partially disposed within the expandable treatment element. The control unit includes a fluid supply reservoir in fluid communication with the expandable treatment element, a pressure sensor configured to monitor a pressure of the expandable treatment element, and processing circuitry. The processing circuitry is configured to initiate and transition between an inflation phase and an ablation phase. The inflation phase includes inflating the expandable treatment element with a refrigerant such that the expandable treatment element is in contact with a target tissue area. The ablation phase includes delivering the refrigerant from the fluid supply reservoir to the expandable treatment element to treat the target tissue area. The processing circuitry is further configured to record a first pressure measurement of the expandable treatment element during the inflation phase and calculate a difference between the first pressure measurement and a predetermined pressure threshold. A first contact score is then assigned based on a comparison of the calculated difference between the first pressure measurement and the predetermined pressure threshold to a predefined scale. The processing circuitry is further configured to record a second pressure measurement of the expandable treatment element during the ablation phase and calculate a difference between the second pressure measurement and the predetermined pressure threshold. A second contact score is then assigned based on a comparison of the calculated difference between the second pressure measurement and the predetermined pressure threshold to a predefined table. The processing circuitry is further configured to determine whether undue force is being applied to the treatment device during at least one of the ablation phase and the inflation phase based, in part, on at least one of the first contact score and the second contact score, and generate an alert if it is determined that undue force is being applied to the treatment device during at least one of the ablation phase and the inflation phase.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The devices, systems, and methods disclosed herein are for treating an area of tissue, such as performing pulmonary vein isolation, spot ablation, and/or linear ablation with a single treatment device. For example, a system is provided that includes a treatment device in communication with a console having a pressure sensor disposed therein. The console is configured to continuously monitor a degree of contact pressure between the balloon element and a target tissue area, which enhances balloon-tissue contact, treatment efficacy, and patient safety.

Figure 1:
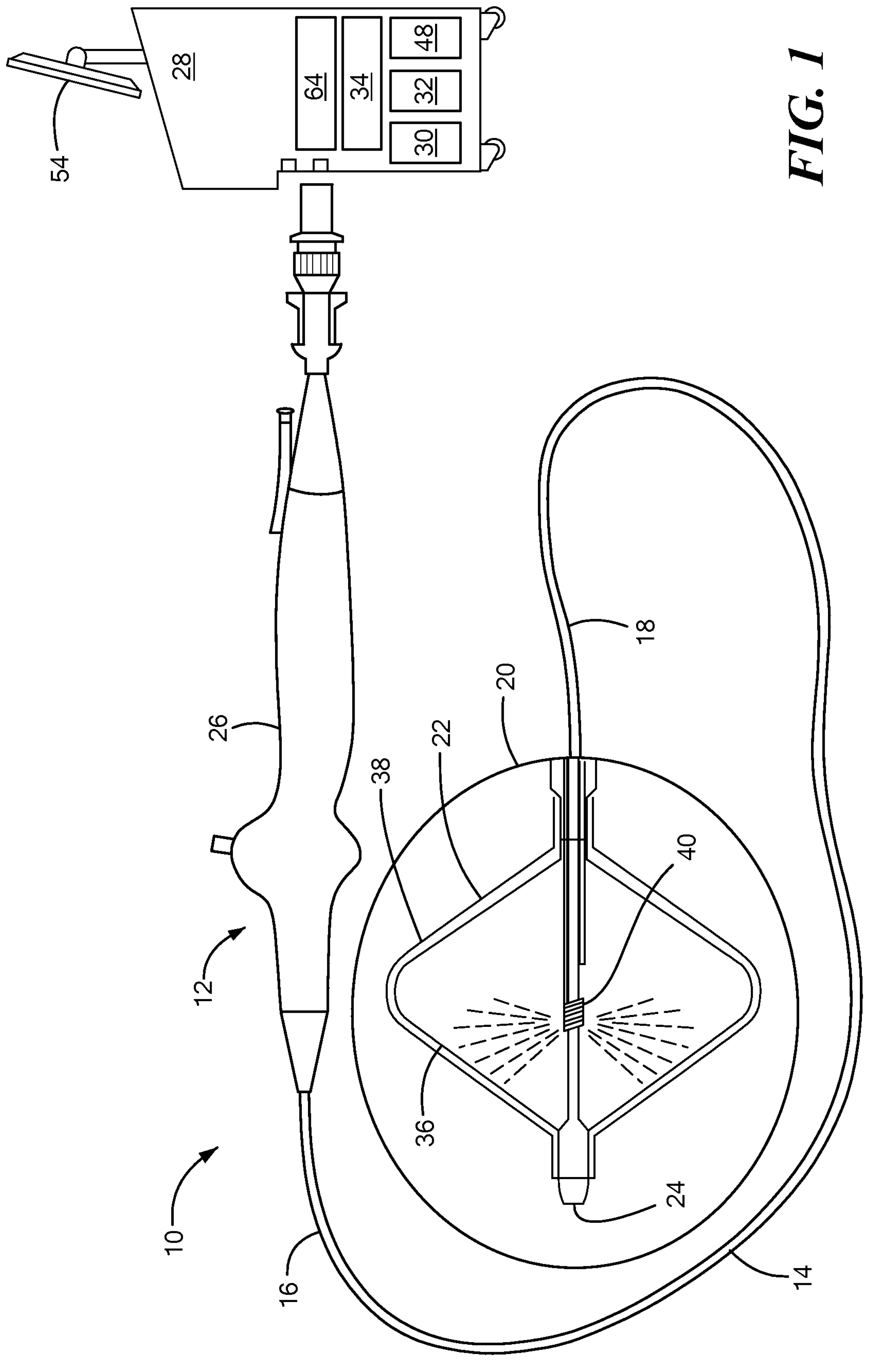
FIG. 1 is schematic illustration of a cryogenic ablation system in accordance with the present invention.

Referring now to the drawing figures in which like reference designations refer to like elements, a first embodiment of a balloon catheter used in conjunction with the present invention is shown in FIG. 1. FIG. 1 shows an exemplary system designated herein by the reference numeral "10" that is suitable for performing cryogenic atrial ablation. The system 10 includes a highly flexible treatment device 12 that is suitable for passage through the vasculature. The treatment device 12 includes an elongate body 14 having a proximal portion 16 and a distal portion 18 opposite the proximal portion 16. The distal portion 18 includes a distal end 20 with an expandable treatment element 22 coupled at or proximal to the distal end 20. The distal end 20 and the expandable treatment element 22 are shown magnified and are described in greater detail below. The distal portion 18 may also define a distal tip 24 defining an aperture (not shown) sized to allow for the passage of a guide wire through the elongate body distal portion 18 and through the aperture. The proximal portion 16 of the treatment device 12 is mated to a handle 26 that can include an element such as a lever or knob for manipulating the elongate body 14 and the treatment element 22.

Continuing to refer to FIG. 1, the handle 26 can also include connectors that are matable directly to a cryogenic fluid supply/exhaust and control unit or indirectly by way of one or more umbilicals (not shown). In the exemplary system the fluid supply and exhaust, as well as various control mechanisms for the system are housed in a single control unit or console 28. In one embodiment, the console 28 may include a fluid supply reservoir 30, an exhaust chamber 32, and processing circuitry 34 configured to monitor and control the delivery and/or exhaust of inflation and/or ablation fluid from the treatment device 12. For example, during inflation of the treatment element 22, refrigerant may be delivered from the fluid supply reservoir 30 in either a gaseous or liquid state towards the treatment element 22. During the ablation phase, refrigerant is delivered towards the treatment element 22 in a liquid state. In addition to providing an exhaust function for the treatment device fluid supply, the console 28 can also recover and/or recirculate the cooling fluid. As such, the system 10 may be referred to herein as a closed-loop system.

Figure 2:
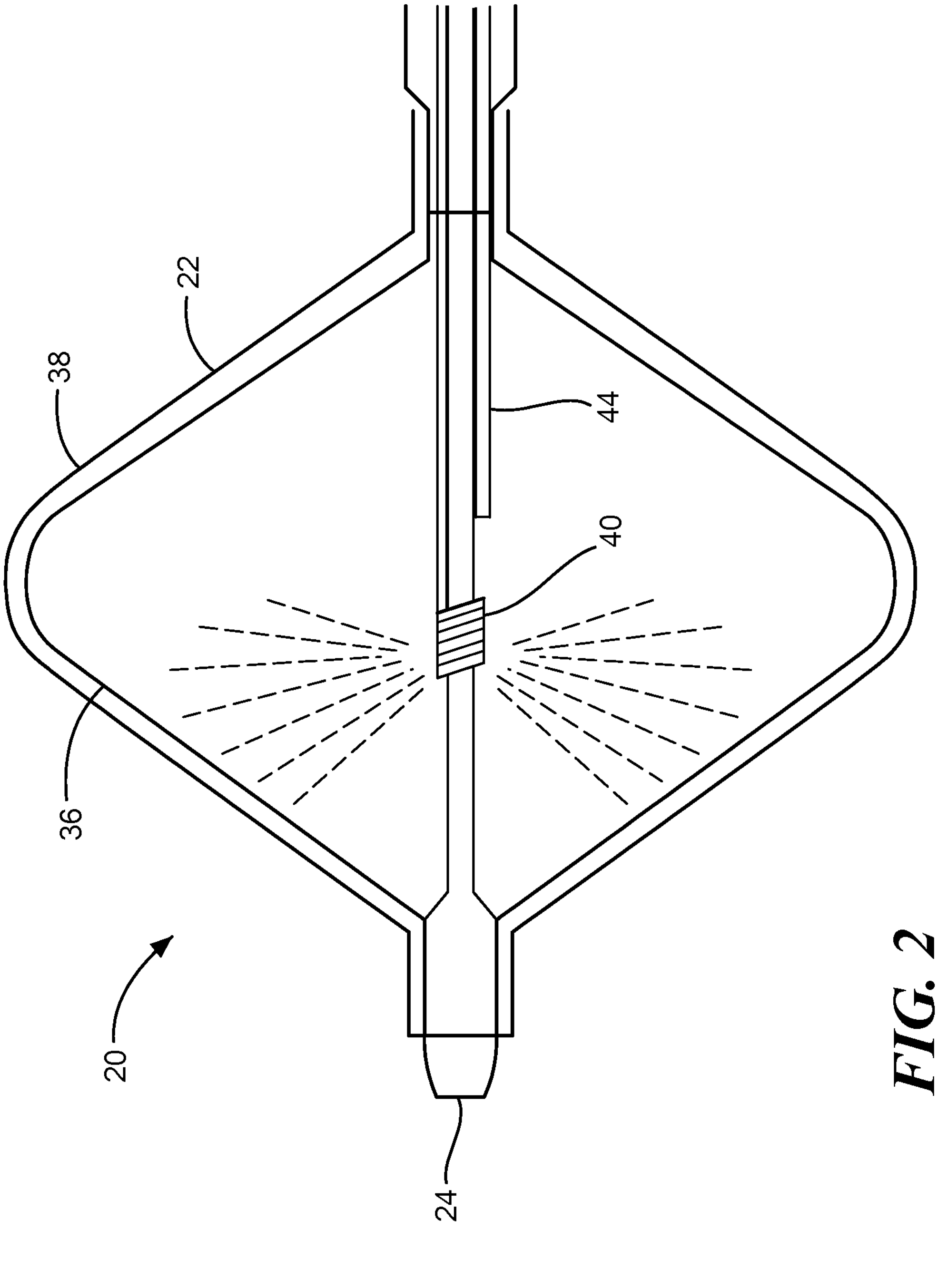
FIG. 2 illustrates the treatment device of FIG. 1, including a pressure monitoring tube located in an expandable treatment element of the treatment device.
Figure 3:
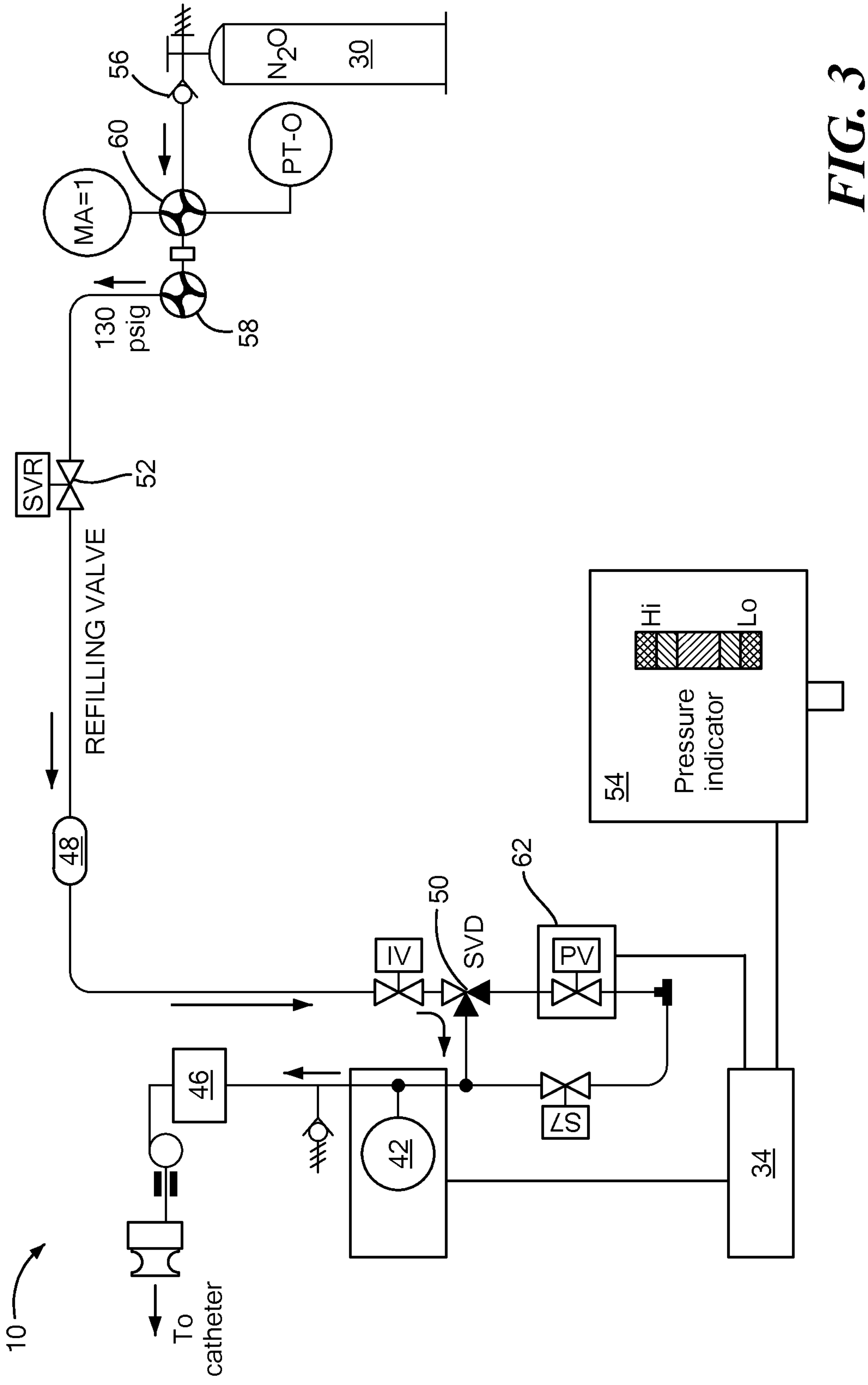
FIG. 3 illustrate a cryoablation system incorporating various embodiments of the apparatus and method of the present invention.

Referring to FIGS. 1-3, the expandable treatment element 22 is shown as a double balloon, wherein an inner balloon 36 is contained by an outer balloon 38. A fluid delivery conduit 40 in fluid communication with the fluid supply reservoir 30 in the console 28 is provided to release refrigerant from one or more openings in the tube within the inner balloon 36 in response to console commands and other control input. A vacuum pump in the console 28 creates a low pressure environment in one or more lumens within the elongate body 14 so that refrigerant is drawn into the lumen(s), away from the inner balloon 36, towards the proximal portion 16 of the elongate body 14, and into the exhaust chamber 32 within the console 28. The vacuum pump is also in fluid communication with the interface of the inner and the outer balloons 36, 38 so that any fluid that leaks from the inner balloon 36 is contained and aspirated. In one embodiment, the console 28 includes one or more pressure sensors 42 (as shown in FIG. 3) along the supply or inflation line to continuously record the instantaneous pressure values within one or both of the balloons 36, 38. The pressure sensors 42 may then generate and transmit a pressure signal to the processing circuitry 34 of the console 28. When refrigerant is released into the inner balloon 36, the inner and the outer balloons 36, 38, expand to a predetermined shape to present an ablation surface, wherein the temperature of the ablation surface is determined by the material properties of the specific refrigerant selected for use, such as nitrous oxide, along with the pressure within the inner balloon 36 and the refrigerant/fluid flow rate. Further, it is contemplated that device 12 may also include a pressure monitoring tube 44 inside the inner balloon 36 (as shown in FIG. 2) or a pressure sensor 42 within the balloon 22 (not shown). The pressure monitoring tube 44 within balloon 36 or sensor 42 within the balloon 22 may be in communication with the console 28 and continuously record the instantaneous pressure values within the balloons.

Further, the system 10 may also include the use of a flow sensor 46 to monitor how much refrigerant is flowing into the balloon 36. The flow sensor 46, shown in FIG. 3, may be included on the inflation line within the console 28 and is configured to measure the rate or speed of fluid or gas at a certain location. An exemplary embodiment of flow sensor 46 is the Microbridge Mass Air Flow Sensor by Honeywell®.

Refrigerant is provided by a refrigerant source within console 28. Refrigerant, typically $N_2O$, passes through the internal piping of console 28 before being transferred to treatment device 12 via the coaxial umbilical (not shown). At the distal end of the umbilical, inside treatment device 12, the refrigerant is released inside the treatment device tip cavity, which is under vacuum. As a result, the temperature of the liquid drops because of the positive Joule-Thomson coefficient of $N_2O$. Then the liquid evaporates as it absorbs heat from the balloon which results in the catheter tip or balloon freezing. The refrigerant vapor is then returned through the vacuum path via the umbilical and into console 28, where it is evacuated through a scavenging line.

In an exemplary use, the console 28 may be used for operating a medical device, such as the treatment device 12, through an inflation phase and ablation phase. Prior to positioning treatment device 12 on the ablation site, the clinician must first insert and navigate the treatment device 12 within the patient's vasculature until the device 12 reaches a location proximate to an area of target tissue within the heart chamber. The clinician may then inflate the treatment element 22 inside the heart chamber until the inner balloon 36 reaches a desired internal pressure. During this phase, the system is under vacuum and provides verification for leaks between the treatment element 22 and the blood and/or between the inner balloon 36 and the outer balloon 38. The ablation site may be referred to herein as an area of target tissue within the left atrium of the heart of a patient. During the inflation phase, the expandable treatment element 22 is inflated by injection fluid or gas through the umbilical under a fixed flow pressure. This ensures a defined and constant pressure inside the balloon 36 in order to provide a mechanical force for inflation. In one embodiment, refrigerant is transferred from the fluid supply reservoir 30 to a second fluid reservoir 48, which delivers a pre-established volume of refrigerant in vapor phase to the treatment device 12, and subsequently to the treatment element 22. The refrigerant transfer may be achieved by having the valve 50 in a closed position, while opening valve 52, thereby placing the fluid supply reservoir 30 in fluid communication with the second fluid reservoir 48 rather than the supply line of the console 28. Once the second fluid reservoir 48 has been adequately filled with refrigerant to a desired level, the refrigerant from the second fluid reservoir 48 may then be transferred along the supply line towards the treatment device 12.

FIG. 3 illustrates the inflation portion of the console mechanics of FIG. 1. The pressure sensor 42, located on the inflation/supply line within the console 28, continuously monitors the pressure inside of the balloon as it is inflated. The pressure sensor 42 is configured to continuously measure the internal pressure of the treatment element 22 that may fluctuate due to balloon deformation caused by the pressure applied on the target tissue by the treatment element 22. Also, in one embodiment, flow sensor 46 may be included on the inflation line within the console 28 to measure the rate of flow of the refrigerant to the treatment element 22 during the inflation phase and may also service as another way to measure balloon deformation caused by the pressure applied on the tissue by the treatment element 22. For example, when the treatment element 22 is pushed against the target tissue and/or any surrounding or collateral structures, an increase in the monitored pressure occurs. In one embodiment, the initial inflation pressure may be about 0.2-2 psig. Once the desired pressure is achieved within the inflated treatment element 22, the flow of refrigerant to the treatment device 12 is stopped by closing solenoid valves 50 and 52 in series, and thereby causing the gas system to become static.

Continuing to refer to FIG. 3, during the inflation of the treatment element 22, the pressure sensor 42 continuously and/or periodically records a first internal pressure measurement of the treatment element 22 and transmits a low frequency pressure measurement signal to the console 28. In one embodiment, the pressure measurement signal may vary proportionally to the internal pressure of the treatment element 22 and may be a DC signal or fixed sinusoidal carrier signal (e.g., up to 10 kHz) that is amplitude modulated by the change in pressure with a change in voltage. Additionally, although not described herein in detail, the pressure measurement signal may also be converted to a digital signal in the handle 26 of the device 12 before being transmitted to the console 28.

Once the console 28 receives the internal pressure measurement signal from the pressure sensor 42, the console 28 then compares the first pressure measurement to a predetermined pressure threshold. The predetermined pressure threshold may be a predetermined balloon pressure range that allows for safe use of the treatment element 22 such that the risk of bursting, leaks, tissue damage or other adverse events is low. The console then calculates a difference between the first pressure measurement and the predetermined pressure threshold to determine how much the first pressure measurement may deviate from the threshold pressure. Once the difference is calculated, the processing circuitry 34 assigns a first contact score that may be displayed as a numerical value or a color-coded symbol on an external display 54. The contact score is indicative of a quality of tissue contact by the balloon during the inflation phase, and is determined by comparing the calculated difference between the first pressure measurement and the predetermined threshold to a predefined table, scale, log, or other set of values. For example, as shown in Table 1 below, if the first pressure measurement deviates more than 1 psia from the predetermined pressure threshold, whether higher or lower, this may indicate inadequate, or poor, tissue contact. Inadequate tissue contact may be the result of the balloon pressure being too high (too much pressure exerted on tissue) or too low (not enough contact with tissue). In situations where the pressure is too high, the excess pressure may cause the treatment element 22 to offset or otherwise moved away from the desired treatment location, as well as deform tissue, which may bring the treatment element 22 closer to and damaging collateral structures (e.g., phrenic nerve, esophagus), thus increasing the risk of potential adverse events. If the first pressure measurement deviates between 0.2 and 1 psia from the predetermined thresholds, this may indicate marginal tissue contact. Marginal tissue contact may be due to contact force or pressure on the treatment element 22 that is slightly too high or too low but less than the contact force or pressure indicating inadequate tissue contact Lastly, if the first pressure measurement deviates less than 0.2 psia from the predetermined threshold, this may indicate adequate tissue contact.

TABLE 1

Measured Pressure ($P_m$) Used to Determined Degree of Tissue Contact

| Deviation of Measured Pressure ($P_m$) From Predetermined Pressure Threshold | Degree of Tissue Contact |
|---|---|
| More than 1 psia | Inadequate Tissue Contact |
| Between 0.2 and 1 psia | Marginal Tissue Contact |
| Less than 0.2 psia | Adequate Tissue Contact |

Figure 4:
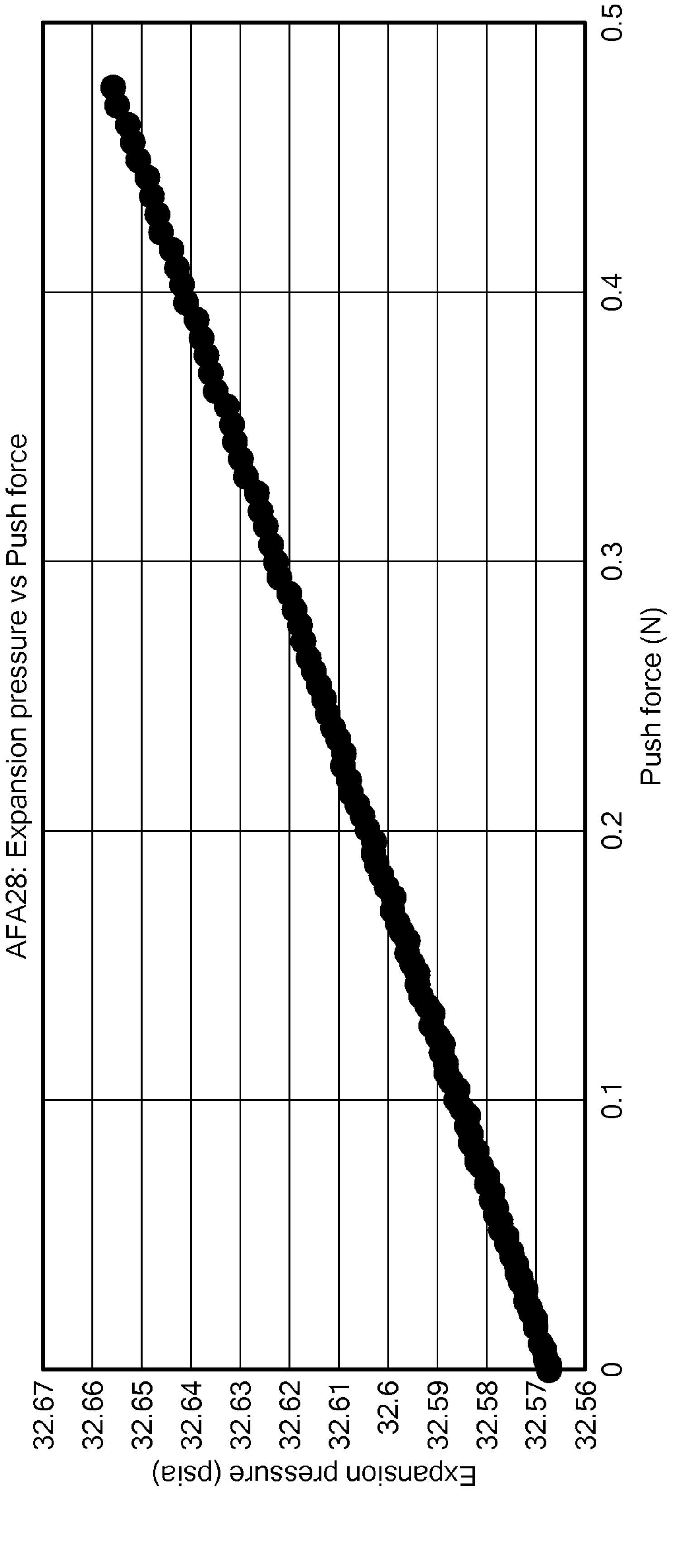
FIG. 4 illustrates a correlation between expansion pressure of the balloon and force exerted on the treatment device.

In another embodiment, if the first pressure measurement is greater than 28.5 or less than 27.5 psia, this may indicate inadequate tissue contact. If the first pressure measurement is between the range of 28.4 and 28.5 psia or 27.5 and 28.2 psia, this may indicate marginal tissue contact. Lastly, if the first pressure measurement is between the range of 28.2 and 28.4 psia, this may indicate adequate tissue contact. By displaying the contact score (i.e., inadequate, adequate, marginal) on the display 54, the clinician may determine whether the device 12 needs to be repositioned or whether the delivery of inflation fluid to the treatment element 22 needs to be adjusted or stopped. As shown in FIG. 4, an increase in expansion pressure of the treatment element 22 may be the result of increased force being applied to the treatment device 12.

As described above, adequate tissue contact between the treatment element 22 and the target tissue may be, for example, a degree of contact between the treatment element 22 and the target tissue in which not too much pressure is being exerted on the tissue by the balloon (which may, for example, be caused by the clinician exerting excessive pressure on the device 12) or in which not too little pressure is exerted such that full contact between the treatment element 22 and target tissue is not achieved. In one embodiment, the contact score is shown as a color-coded symbol. For example, the first contact score may be indicated as a red symbol which alerts the clinician as to a inadequate or low degree of contact between the treatment element 22 and the target tissue. When the symbol is yellow, this may indicate a moderate or marginal degree of contact between the treatment element 22 and the target tissue. Lastly, when the symbol is green, this may indicate a adequate or higher degree of contact between the treatment element 22 and the target tissue in which the balloon pressure is presently within the predetermined threshold range. The console 28 may be coupled to the display 54 so that the assigned first contact score may be displayed to a clinician during the treatment procedure, thereby improving patient safety and treatment efficacy by making the clinician aware as to the degree of contact between the treatment element 22 and the area of target tissue. By making clinicians aware as to the quality of contact between the treatment element 22 and the area of target tissue, clinicians would then have the opportunity to make positioning adjustments and/or balloon pressure/flow adjustments so that a more desirable degree of contact between the treatment element 22 and the target tissue can be achieved prior to the ablation phase. After the treatment element 22 has achieved the desired inflation pressure and degree of tissue contact, and after the console 28 has displayed the generated the first contact score on the display 54, the inflation phase may be stopped, and the ablation phase may begin. It is to be understood that the system described herein is not limited to the colors described above (i.e., green, yellow, red) and thus any colors may be used by the color-coded system to distinguish between varying levels of tissue contact by the treatment element 22.

The ablation phase generally includes providing refrigerant flow to the treatment device 12 at the target refrigerant flow rate such that the desired thermal treatment may be provided to the target tissue. For example, the particular treatment may include the ablation of tissue, which may be achieved by the temperature resulting in a portion of the medical device due to the refrigerant being circulated within the treatment element 22. In other words, during the ablation phase, the console 28 is configured to initiate the circulation of refrigerant within the treatment element 22. The refrigerant is circulated within the treatment element 22 at a temperature sufficient to cryoablate the target tissue area. For example, the refrigerant may cool the treatment element 22 such that the treatment element 22 extracts heat from or otherwise cools the target tissue such that the tissue is ablated by the treatment of thermal energy. A transition mode follows inflation but precedes ablation. In the case of cyrogenic ablation systems, a transition method is needed to transition from closed pressurized volume to an open circuit, which allows the flow of refrigerant to enter and exit the catheter tip while at the same time controlling the balloon pressure in order to keep the balloon inflated and in place. During the transition, a pressure switch, which is adjusted to a pressure higher than atmospheric pressure but preferably lower than 20 psia, monitors the pressure inside the treatment device 12. The solenoid valve 50 remains closed until the pressure in the treatment device is higher than the preset switch value after which the solenoid valve opens to allow evacuation of excess refrigerant. When the pressure falls below the reset switch value, the solenoid valve 50 closes to keep the balloon inflated and above atmospheric pressure. During the transition, ablation is already initiated but the pressure switch controls the balloon pressure until refrigerant flow alone maintains the balloon open and above atmospheric pressure. The transition phase is considered complete when certain conditions are met: 1) when the pressure switch commands the solenoid valve 50 to open to vacuum and the balloon pressure remains above the present switch value; 2) the duration of the transition phase exceeds a predetermined time; and 3) the injection pressure reaches a predetermined value that is adequate to generate enough flow to maintain the balloon open.

During the ablation phase, refrigerant is injected through the umbilical system into the treatment element 22. When injection of refrigerant is desired, $N_2O$ gas is released from the fluid supply reservoir 30 and/or second fluid reservoir 48 and provides high pressure liquid through a check valve 56 and a series of pressure regulators 58 and 60. Regulators 58 and 60 are primary and secondary pressure regulators respectively, which serve to measure and bring the gas pressure down to between 810 and approximately 840 psia. The proportional valve 62 is used to regulate and vary the pressure inside the injection line based on refrigerant flow and treatment element 22 pressure feedback. This in turn will further vary the flow rate of refrigerant to the catheter tip. An increase in the flow rate (less restriction by the regulator) lowers the temperature of the treatment element 22. Conversely, decreasing the flow rate allows the treatment element 22 to be warmed by its surroundings.

Further, the pressure sensor 42 is configured to record a second pressure measurement of the treatment element 22 during the ablation phase and transmit the recorded second pressure measurement to the processing circuitry 34 of the console 28. The processing circuitry 34 then compares and calculates a difference between the second pressure measurement and the predetermined pressure threshold to determine how much the second pressure measurement deviates from the predetermined pressure threshold. Similar to the inflation phase, the processing circuitry 34 then compares the calculated difference to the predefined table, scale, log, or set of value to determine a second contact score that should be assigned to the calculated difference. Similar to the first contact score, the second contact score may also be a numerical value or a color-coded symbol, and is determined in the same manner as described above in reference to the first contact score and using the predefined table as shown in Table 1. However, the assigned second contact score is indicative of a degree of tissue contact by the treatment element 22 during the ablation phase.

It is to be understood that the first and second contact scores may also provide actionable data that allows the clinician to adjust the force applied to the treatment device 12 for enhanced tissue contact and/or to avoid the risk of patient injury by applying too much force on the target tissue and any surrounding structures. Once the console 28 has assigned at least one of the first contact score and the second contact score, the console 28 may then also determine whether undue force is being applied to the treatment device 12 and/or target tissue during the inflation and/or ablation phases based, in part, on at least one of the first contact score and the second contact score. For example, when either the first or second contact scores indicate inadequate tissue contact, it may be the result of undue force being applied to the device 12. Undue force may be an adverse event that results from excessive pressure being applied to the target tissue by the balloon 22, which may lead to patient injury, abnormal ablation patterns, undesired damage to target tissue and/or collateral tissue structures, and/or damage to the treatment element 22 (i.e., balloon bursting, leaks, etc.). Additionally, although not described in detail herein, it is to be understood that other adverse events other than undue force may also be determined by an analysis of the first and/or second contact scores. The processing circuitry 34 is further configured to generate an alert if it is determined that undue force is being applied to the treatment device during at least one of the ablation phase and the inflation phase. The alert may be an audio and/or visual message or alarm that is relayed to a clinician via the display 54. In one embodiment, the alert may provide a recommendation to, or may be a signal to the clinician to, adjust a flow rate of the refrigerant and/or discontinue the delivery of refrigerant in response to the detection of undue force during the at least one of the ablation phase and the inflation phase. The alert may also warn the clinician to reposition the device 12 at the target tissue area.

Figure 5A:
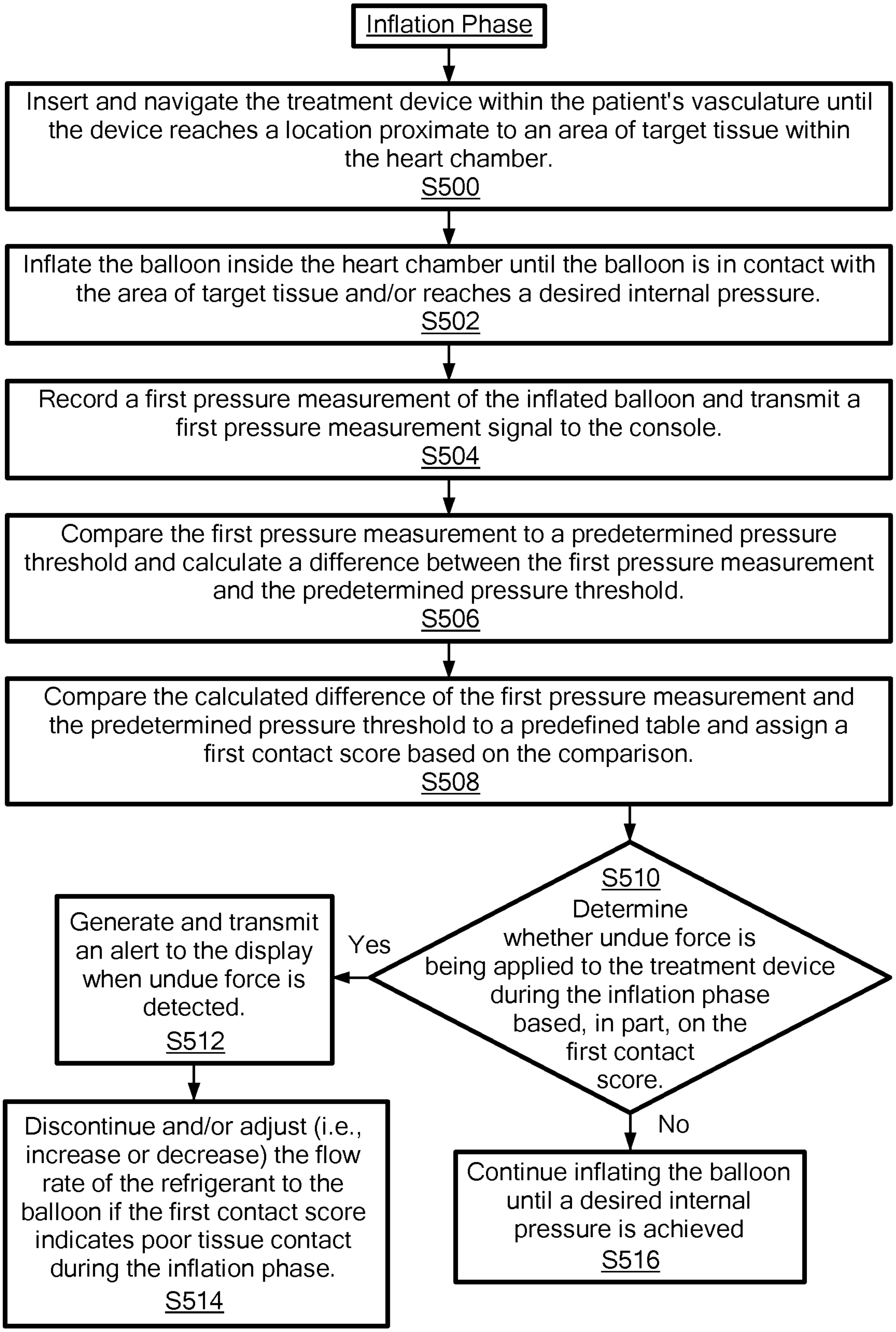
FIG. 5A is a flow chart of an exemplary use of a control console in accordance with the present invention during an inflation phase.
Figure 5B:
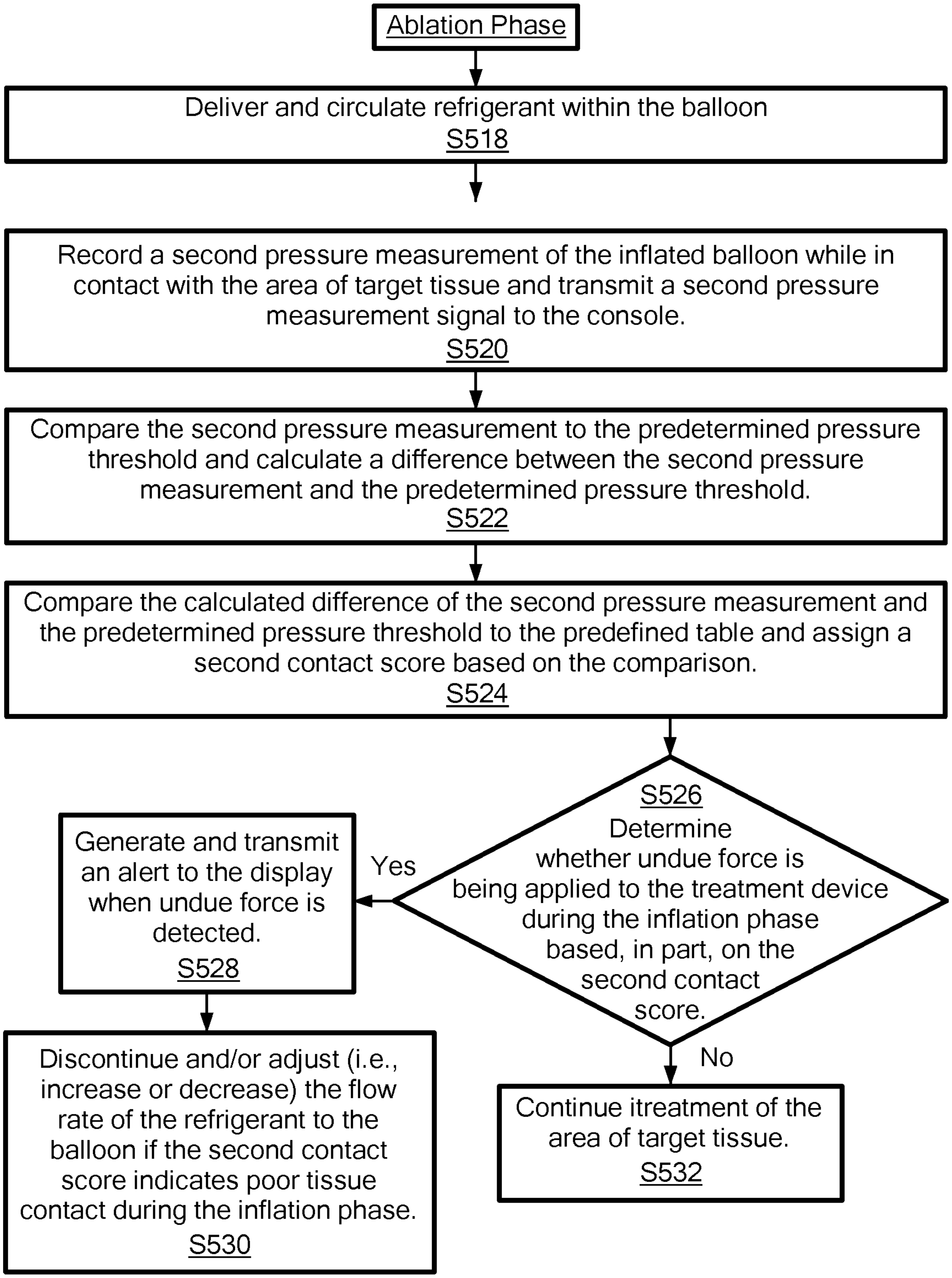
FIG. 5B is a flow chart of an exemplary use of a control console in accordance with the present invention during an ablation phase.

Now referring to FIGS. 5A-5B, an exemplary method of the system 10 described herein is shown in a flow chart. Prior to positioning treatment device 12 on the ablation site, the clinician must first insert and navigate the treatment device 12 within the patient's vasculature until the device 12 reaches a location proximate to an area of target tissue within the heart chamber (S500). The clinician may then inflate the treatment element 22 inside the heart chamber until the treatment element 22 is in contact with the area of target tissue and/or reaches a desired internal pressure (S502). Once in contact with the area of target tissue, the pressure sensor 42 records a first pressure measurement of the inflated treatment element 22 and transmits a first pressure measurement signal to the processing circuitry 34 of the console 28 (S504). Once received by the console 28, the processing circuitry 34 then compares the first pressure measurement to a predetermined pressure threshold and calculates a difference between the first pressure measurement and the predetermined pressure threshold (S506). The processing circuitry 34 may then compare the calculated difference of the first pressure measurement and the predetermined pressure threshold to a predefined table, scale, log, or set of values stored within the memory 64 of the console 28, and generate and/or assign a first contact score based on the comparison (S508). The assigned first contact score may be indicative of a degree or quality of tissue contact by the balloon 22 during the inflation phase. The assigned first contact score may be continuously displayed on the display 54 for indicating the degree or quality of tissue contact to the clinician during the procedure. Further, the processing circuitry 34 may then determine whether undue force is being applied to the treatment device during the inflation phase based, in part, on the first contact score (i.e., inadequate tissue contact) (S510). For example, if the first contact score indicates an inadequate level or degree of tissue contact, an alert may be generated and transmitted to the display where it may then be used to notify the clinician to adjust the positioning of the balloon 22 or the pressure within the treatment element 22 during the inflation phase (S512). In response to the alert, the clinician may then discontinue or adjust (i.e., increase or decrease) the flow rate of the refrigerant to the treatment element 22 if the first contact score indicates inadequate tissue contact during the inflation phase (S514). However, if undue force is not detected, the inflation of the treatment element 22 will continue until the treatment element 22 in contact with the area of target tissue and/or until a desired internal balloon pressure is achieved (S516).

Once the treatment element 22 has been inflated, and the first pressure measurement has been recorded, refrigerant may then be delivered to and circulated within the treatment element 22 during an ablation phase (S518). The refrigerant may be circulated within the treatment element 22 until the temperature of the treatment element 22 is reduced to a temperature sufficient to cryoablate the area of target tissue. During this ablation phase, the pressure sensor 42 records a second pressure measurement of the treatment element 22 while in contact with the area of target tissue and transmits a second pressure measurement signal to the processing circuitry 34 of the console 28 (S520). Once received by the console 28, the processing circuitry 34 then compares the second pressure measurement to the predetermined pressure threshold and calculates a difference between the second pressure measurement and the predetermined pressure threshold (S522). The processing circuitry 34 may then compare the calculated difference of the second pressure measurement and the predetermined pressure threshold to the predefined table, scale, log, or set of values stored within the memory 64 of the console 28, and generate and/or assign a second contact score based on the comparison (S524). The assigned second contact score may be indicative of a degree or quality of tissue contact by the balloon 22 during the ablation phase. The assigned second contact score may be continuously displayed on the display 64 for indicating the degree or quality of tissue contact to the clinician during the procedure. Further, the processing circuitry 34 may then determine whether undue force is being applied to the treatment device during the ablation phase based, in part, on the second contact score (S526). For example, if the second contact score indicates a inadequate level or degree of tissue contact, a second alert may be generated and transmitted to the display 54 where it may then be used to notify the clinician to adjust the positioning of the balloon 22 or the pressure within the treatment element 22 during the ablation phase (S528). In response to the alert, the clinician may then discontinue or adjust (i.e., increase or decrease) the flow rate of the circulated refrigerant if the second contact score indicates inadequate tissue contact during the ablation phase (S530). However, if undue force is not detected, the treatment procedure may continue until a desired lesion, lesion pattern, or ablative effect is achieved (S532).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of ablating tissue, the method comprising:

positioning a treatment device proximate to a target tissue area, the treatment device having an expandable treatment element;

inflating the expandable treatment element with a refrigerant during an inflation phase such that at least a portion of the expandable treatment element is in contact with the target tissue area;

recording a first pressure measurement within the inflated expandable treatment element during the inflation phase and comparing the first pressure measurement to a predetermined pressure threshold;

circulating the refrigerant within the expandable treatment element during an ablation phase to reduce a temperature of the target tissue area to a temperature sufficient to cryoablate the target tissue area;

recording a second pressure measurement within the inflated expandable treatment element during the ablation phase and comparing the second pressure measurement to the predetermined pressure threshold;

calculating a difference between the first pressure measurement and the predetermined pressure threshold; and assigning a first contact score based on the calculated difference, the assigned first contact score being indicative of a quality of tissue contact by the expandable treatment element during the inflation phase.

2. The method of claim 1, further comprising:

calculating a difference between the second pressure measurement and the predetermined pressure threshold; and assigning a second contact score based on the calculated difference between the second pressure measurement and the predetermined pressure threshold, the assigned second contact score being indicative of a quality of tissue contact by the expandable treatment element during the ablation phase.

3. The method of claim 2, further including:

determining whether undue force is being applied to the treatment device during at least one of the ablation phase and the inflation phase based, in part, on at least one of the first contact score and the second contact score.

4. The method of claim 3, further comprising:
generating an alert if it is determined that undue force is being applied to the treatment device during at least one of the ablation phase and the inflation phase.

5. The method of claim 3, further comprising at least one selected from the group consisting of:
adjusting a flow rate of the refrigerant if it is determined that undue force is being applied to the treatment device during at least one of the ablation phase and the inflation phase; and
discontinuing the circulation of the refrigerant if it is determined that undue force is being applied to the treatment device during at least one of the ablation phase and the inflation phase.

6. The method of claim 2, further including:
determining whether the second contact score is indicative of inadequate tissue contact;
generating an alert if the second contact score indicates inadequate tissue contact during the ablation phase; and
at least one of adjusting a flow rate of the refrigerant and discontinuing the circulation of the refrigerant if the second contact score indicates inadequate tissue contact during the ablation phase.

7. A system for ablating tissue, comprising:
a treatment device including an expandable treatment element and a pressure monitoring tube having a proximal portion and an opposite distal portion, the distal portion being partially disposed within the expandable treatment element;
a control unit in communication with the treatment device, the control unit including processing circuitry configured to:
initiate and transition between an inflation phase and an ablation phase;
record a first pressure measurement of the expandable treatment element during the inflation phase and compare the first pressure measurement to a predetermined pressure threshold;
record a second pressure measurement of the expandable treatment element during the ablation phase and compare the second pressure measurement to the predetermined pressure threshold;
calculate a difference of the first pressure measurement and the second pressure measurement from the predetermined pressure threshold;
assign a first contact score based on a comparison of the calculated difference between the first pressure measurement and the predetermined pressure threshold to a predefined table; and
assign a second contact score based on a comparison of the calculated difference between the second pressure measurement and the predetermined pressure threshold to the predefined table.

8. The system of claim 7, wherein the control unit further includes:
a fluid supply reservoir in fluid communication with the expandable treatment element; and
a pressure sensor configured to monitor a pressure of the expandable treatment element.

9. The system of claim 8, wherein the inflation phase includes inflating the expandable treatment element such that the expandable treatment element is in contact with a target tissue area.

10. The system of claim 9, wherein the ablation phase includes delivering the refrigerant from the fluid supply reservoir to the expandable treatment element to treat the target tissue area.

11. The system of claim 7, wherein the processing circuitry is further configured to:
determine whether undue force is being applied to the treatment device during at least one of the ablation phase and the inflation phase based, in part, on at least one of the first contact score and the second contact score.

12. The system of claim 11, wherein the processing circuitry is further configured to generate an alert if it is determined that undue force is being applied to the treatment device during at least one of the ablation phase and the inflation phase.

13. The system of claim 12, wherein the processing circuitry is further configured to perform one operation selected from the group consisting of:
adjust a flow rate of the refrigerant if undue force is being applied to the treatment device during the at least one of the ablation phase and the inflation phase; and
discontinue the delivery of the refrigerant if undue force is being applied to the treatment device during the at least one of the ablation phase and the inflation phase.

14. The system of claim 11, wherein the processing circuitry is further configured to determine whether at least one of the first contact score and the second contact score is indicative of inadequate tissue contact.

15. The system of claim 14, wherein the processing circuitry is further configured to:
generate an alert if the at least one of the first contact score and the second contact score indicates inadequate tissue contact during at least one of the ablation phase and the inflation phase; and
at least one of adjust a flow rate of the refrigerant and discontinue the circulation of the refrigerant if the at least one of the first contact score and the second contact score indicates inadequate tissue contact during at least one of the ablation phase and the inflation phase.

16. A system for ablating tissue, comprising:
a treatment device including an expandable treatment element and a pressure monitoring tube having a proximal portion and an opposite distal portion, the distal portion being partially disposed within the expandable treatment element;
a control unit in communication with the treatment device, the control unit including:
a fluid supply reservoir in fluid communication with the expandable treatment element;
a pressure sensor configured to monitor a pressure of the expandable treatment element; and
processing circuitry configured to:
initiate and transition between an inflation phase and an ablation phase, the inflation phase including inflating the expandable treatment element with a refrigerant such that the expandable treatment element is in contact with a target tissue area, the ablation phase including delivering the refrigerant from the fluid supply reservoir to the expandable treatment element to treat the target tissue area;
record a first pressure measurement of the expandable treatment element during the inflation phase;
calculate a difference between the first pressure measurement and a predetermined pressure threshold;
assign a first contact score based on a comparison of the calculated difference between the first pressure measurement and the predetermined pressure threshold to a predefined scale;

record a second pressure measurement of the expandable treatment element during the ablation phase;

calculate a difference between the second pressure measurement and the predetermined pressure threshold;

assign a second contact score based on a comparison of the calculated difference between the second pressure measurement and the predetermined pressure threshold to a predefined table;

determine whether undue force is being applied to the treatment device during at least one of the ablation phase and the inflation phase based, in part, on at least one of the first contact score and the second contact score; and generate an alert if it is determined that undue force is being applied to the treatment device during at least one of the ablation phase and the inflation phase.

* * * * *